United States Patent

Obana et al.

Patent Number: 5,500,454
Date of Patent: Mar. 19, 1996

[54] DENTURE BASE SEPARATING MATERIAL

[75] Inventors: Jinichi Obana; Shigeru Hanatani; Junichi Okada; Yukari Nasu; Ryoji Nakazato, all of Tokyo, Japan

[73] Assignee: GC Corporation, Tokyo, Japan

[21] Appl. No.: 309,547

[22] Filed: Sep. 20, 1994

Related U.S. Application Data

[62] Division of Ser. No. 229,430, Apr. 12, 1994, abandoned.

[30] Foreign Application Priority Data

Apr. 26, 1993 [JP] Japan ................................. 5-120461

[51] Int. Cl.$^6$ ............................. A61K 6/02; C08L 33/10
[52] U.S. Cl. ........................ 523/120; 523/109; 427/2.29; 433/168.1; 524/556; 524/560; 524/561; 524/565
[58] Field of Search .................... 524/556, 560, 524/561, 565; 433/168.1; 523/120, 109; 427/2

[56] References Cited

U.S. PATENT DOCUMENTS

| | | | |
|---|---|---|---|
| 2,446,298 | 8/1948 | Nelson | 523/120 |
| 4,145,412 | 3/1979 | Ladanyi | 424/58 |
| 4,685,931 | 8/1987 | Schieferstein | 524/560 |
| 4,925,908 | 5/1990 | Bernard | 526/318.4 |
| 5,075,107 | 12/1991 | Katakura et al. | 523/120 |
| 5,231,145 | 7/1993 | Brueckmann | 526/318.4 |
| 5,250,609 | 10/1993 | Kato | 526/318.44 |
| 5,268,437 | 12/1993 | Holy | 526/318.4 |
| 5,286,764 | 2/1994 | Prosise | 523/120 |

*Primary Examiner*—Paul R. Michl
*Assistant Examiner*—Andrew E. C. Merriam
*Attorney, Agent, or Firm*—Oblon, Spivak, McClelland, Maier, & Neustadt

[57] ABSTRACT

A denture base separating material is disclosed, comprising an aqueous emulsion obtained by emulsion polymerization of methacrylic ester, acrylic ester, or acrylonitrile alone, or a mixed solution of two or more thereof, in the presence of a water-soluble radical polymerization initiator and a surfactant, the monomer composition of which is adjusted such that the minimum film-forming temperature is 23° C. or lower having an appropriate adhesion and being able to be readily removed from the tissue conditioner, being easily confirmed at the time of application, being from dry spots and cracks on the denture surface, and not generating malodors.

4 Claims, No Drawings

DENTURE BASE SEPARATING MATERIAL

This application is a division of application Ser. No. 08/229,430, filed on Apr. 12, 1994, now abandoned.

FIELD OF THE INVENTION

The present invention relates to a separating material to be used in the dental remedy. In particular, the present invention relates to a denture base separating material which can not only impart a tissue conditioner with an appropriate adhesion to a denture in the oral cavity upon being previously applied to the denture but also make it easy to peel off the tissue conditioner after the use.

BACKGROUND OF THE INVENTION

When a denture is used for a long period of time, the fitness becomes worse due to absorption of the residual ridge and to the change in occlusion, leading to reduction in their retention and stability. And when an unfit denture is used as it is, since a non-uniform occlusal stress is applied to a mucosa below the denture base, a pain may be caused, and an uleur and inflammation are likely generated. For these reasons, it is necessary to recover the fitness of a denture by repair or reproduction of the denture. In the actual clinics, these treatments are carried out by undergoing lining of a soft material called as a tissue conditioner on the mucosal surface of the denture base to improve the mucosa below the denture base. The tissue conditioner which is used at this time is generally composed of a powder comprising a methacrylic ester-based polymer and a liquid containing, as a major component, a plasticizer such as phthalic esters, and these materials are used upon mixing at the time of use. The tissue conditioner must be frequently exchanged at intervals between several days and one week while examining the degree of improvement of the oral mucosa, and such an operation was extremely difficult. Although the tissue conditioner is usually peeled off by means of fingers or a carving knife, or the like, since not only the tissue conditioner is well adhered to the denture, but also the tensile strength of this material is low, it was likely torn off and left on the denture. While the tissue conditioner remained on and adhered to the surface of the denture base is cut off by means of a grinding bur or the like, since this material is a very soft material, it was extremely difficult to completely remove it.

In order to solve these problems, the present inventors made extensive investigations with respect to a separating material for tissue conditioners. Though this separating material can firmly fix a tissue conditioner to a denture during the use, it must be readily peeled off from the denture after the use. In each of the dental fields, vaseline is widely used as the separating material. While the present inventors investigated the use of vaseline as a separating material at the beginning, it was found that this material has the following drawbacks as the separating material.

(1) In the long-term water immersion test at 37° C. on the assumption of the inside of the oral cavity, the separating effect decreases with a lapse of time.

(2) The viscosity is so high that it is difficult to uniformly apply it to the denture. For this reason, the applied surface is likely uneven so that the separability is too good, whereby the tissue conditioner may be dropped from the denture, or it is applied too thin so that no separability may be shown at all.

In the general industrial field, silicone oil is widely used as a separating material. According to experiments made by the present inventors, this did not substantially show a separating effect as a tissue conditioner.

The tissue conditioner contains even 40% by weight of a plasticizer as one of the essential components thereof. Since plasticizers are very compatible with polymeric materials, the plasticizer contained in the tissue conditioner penetrates into silicone oil or vaseline, or is mixed with them, whereby it possibly reaches the denture. Once the tissue conditioner is brought into contact with a methacrylic resin-made denture, since the plasticizer also penetrates into the denture, it can be easily expected that the adhesive force increases with a lapse of time. For this reason, the present inventors considered that one which can form a firm coating film on the denture surface is effective as the separating material.

As one method, if an appropriate polymer is dissolved in an organic solvent and applied to the denture surface, a firm coating film can be formed. However, a methacrylic resin which is a typical material for dentures generates dry spots, cracks and the like due to the presence of organic solvents such as ethanol, acetone, dichloromethane, and toluene. For this reason, even when a polymer having a separating effect is found out, it is extremely difficult to find out a solvent for this polymer, which does not denature the methacrylic resin-made denture. Moreover, the use of these organic solvents in the room is not desired from the standpoints of their inherent malodors, toxicity and inflammability, and the like. With such backgrounds in mind, the present inventors reached the conclusion that one which forms a firm coating film after the application but does not contain an organic solvent as a major component is useful as the denture base separating material.

SUMMARY OF THE INVENTION

The present inventors have continued the extensive investigations based on this thinking. As a result, it has been found that an aqueous emulsion obtained by emulsion polymerization of a methacrylic ester, an acrylic ester, or acrylonitrile alone, or a mixed solution of two or more thereof, in the present of a water-soluble radical polymerization initiator and a surfactant, can be applied.

That is, an object of the present invention is to provide a denture base separating material comprising an aqueous emulsion obtained by emulsion polymerization of a methacrylic ester, an acrylic ester, or acrylonitrile alone, or a mixed solution of two or more thereof, in the presence of a water-soluble radical polymerization initiator and a surfactant.

DETAILED DESCRIPTION OF THE INVENTION

Since the separating material obtained according to the present invention contains water as a solvent, it does not denature a denture but forms a firm coating film on the denture surface so that it can meet both the requirements of separability and retention as a tissue conditioner.

The separating material obtained according to the present invention shows cloudy due to the dispersion of a light inherent to the aqueous emulsion. For this reason, in the case that it is applied to a denture, it is easy to confirm the applied surface. Moreover, since a translucent coating film is obtained after drying by means of an air gun or the like, the degree of drying can also be confirmed.

In general, a minimum temperature at which an aqueous emulsion can form a coating film is called as a minimum film-forming temperature (MFT) (Shintaro KUNISAWA and Masayuki FURUYA, *Emulsion and Latex handbook*, p. 21, Taiseisha). MFT of the denture base separating material according to the present invention must be 23° C. or lower. That is, this is because when the denture base separating material according to the present invention is applied to the surface of the denture base material at room temperature by means of a writing brush or the like, a uniform coating film must be formed. It is known that MFT has a close relationship with the glass transition temperature (Tg) of a polymer contained in an aqueous emulsion (Soichi MUROI, *Chemistry of Polymeric Latexes*, pp. 260–261, Kobunshi Kankokai). Since MFT of the denture base separating material according to the present invention must be 23° C. or lower if the glass transition temperature of the polymer contained therein is too high, a uniform coating film can not be formed at room temperature. For example, aqueous emulsions obtained by polymerizing only monomers, each of which has a glass transition temperature higher than room temperature upon being homopolymerized, such as acrylonitrile, methyl methacrylate, ethyl methacrylate, propyl methacrylate, tertiary butyl methacrylate, isobutyl methacrylate, cyclohexyl methacrylate, and tertiary butyl acrylate, either singly or in admixture of these monomers, can not form a uniform coating film upon being applied to the surface of the denture base material at temperature of 23° C. or lower.

In general, for the purpose of lowering MFT, a plasticizer such as phthalic esters or fatty esters are added to an emulsion. This technology can also be applied to the separating material according to the present invention. However, since the plasticizer added to the separating material penetrates into a methacrylic resin-made denture with a lapse of time, the adhesion of the separating material to the denture increases, whereby the effect of the separating material decreases with a lapse of time. For this reason, the amount of the plasticizer which can be added to the separating material according to the present invention must be controlled to 7 parts or less by weight based on 100 parts by weight of the polymer contained in the separating material. For this reason, with this amount of the plasticizer, it is impossible to control MFT of the aqueous emulsion obtained from methyl methacrylate, acrylonitrile, tertiary butyl methacrylate, or ethyl methacrylate, to 23° C. or lower. In the case that MFT is slightly higher than 23° C. as in an aqueous emulsion of poly-n-butyl methacrylate, this technology is greatly effective.

In this case, as a method for adding the plasticizer to the aqueous emulsion, the methods which are generally carried out can be employed. For example, the plasticizer may be added to the monomer solution before the emulsion polymerization, or the plasticizer may be emulsified by using an appropriate emulsifier after the emulsion polymerization. As another method for lowering MFT of the emulsion, it is known to undergo copolymerization with a monomer which has a lower glass transition temperature upon being homopolymerized (Shintaro KUNISAWA and Masayuki FURUYA, *Emulsion and Latex Handbook*, p. 241, Taiseisha). As described above, it is impossible to prepare aqueous emulsions having an MFT of 23° C. or lower by using only acrylonitrile or ethyl methacrylate. However, if such a monomer is copolymerized with a monomer which has a lower glass transition temperature upon being homopolymerized, it is possible to control MFT to 23° C. or lower. Specifically, the former may be copolymerized with an acrylic ester having, as an ester residual group, a straight alkyl group containing from 3 to 10 carbon atoms, isobutyl acrylate, 2ethylhexyl acrylate, lauryl methacrylate, or tridecyl methacrylate.

As the blending ratio of such a monomer increases, it becomes possible to lower MFT to 23° C. or lower, with Tg of the copolymer contained in the obtained aqueous emulsion being lowered. However, in accordance with experiments made by the present inventors, it has become clear that if the blending ratio of such a monomer excessively increases, while the tissue conditioner can be well separated from the denture, the separability is excessively good so that the tissue conditioner is peeled off from the denture in the oral cavity during use.

Specifically, in the case of copolymerization with a monomer selected from an acrylic ester having, as an ester residual group, a straight alkyl group containing from 3 to 10 carbon atoms, isobutyl acrylate, 2-ethylhexyl acrylate, lauryl methacrylate, and tridecyl methacrylate, the tissue conditioner is peeled off from the denture surface in the oral cavity unless the sum of the molar fractions of these monomers is 0.8 or less.

With respect to methyl acrylate, ethyl acrylate, lauryl acrylate, cyclohexyl acrylate, 2-ethylhexyl methacrylate, n-butyl methacrylate, and the like, each of which has a glass transition temperature of from −20° C. to 20° C. in the case of homopolymerization thereof, a good separating material can be obtained even if such a monomer is not copolymerized with any one of an acrylic ester having, as an ester residual group, a straight alkyl group containing from 3 to 10 carbon atoms, isobutyl acrylate, 2-ethylhexyl acrylate, lauryl methacrylate, and tridecyl methacrylate.

Even with an aqueous emulsion having styrene copolymerized therewith, a separating material can be obtained. However, a malodor inherent to the styrene polymer is so severe that the resulting aqueous emulsion is not suitable for the dental use.

The content of the polymer or copolymer which the separating material according to the present invention contains is also important. Not only it is difficult to polymerize an aqueous emulsion having the content exceeding 55% by weight without coagulation being caused, but the viscosity of the separating material increases so that it is difficult to undergo the application.

On the other hand, if the content is 8% or less by weight, not only the viscosity is excessively lowered so that the application becomes difficult, but since the separating material is repelled depending upon the state of the denture surface, the effect of the separating material may not be thoroughly attained. As a matter of course, the viscosity may be adjusted by adding the separating material with a water-soluble polymeric material such as sodium polyacrylate, methyl cellulose, carboxymethyl cellulose, and polyvinyl alcohol. In the separating material according to the present invention, for the purpose of increasing the storage stability, the technologies to be carried out in order to increase the storage stability of general aqueous emulsions can be used as they are. For example, the polymer contained in the separating material may be imparted with stability by forming a copolymer with a monomer having a carboxyl group or a hydroxyl group, such as acrylic acid, methacrylic acid, hydroxyethyl methacrylate, and hydroxypropyl methacrylate, or sodium 2-sulfoethyl methacrylate or 2-aminoethyl methacrylate hydrochloride. These monomers are used in an amount of from about 0.01 to 0.16 in terms of the molar fraction to the mixed solution of the monomers added at the time of the aqueous emulsion polymerization. Also, in the case of copolymerization with a monomer having a carboxyl group, the viscosity of the separating material may be increased by adding base such as ammonia water.

The present invention will be specifically described with respect to the following examples.

In these examples, while sodium lauryl sulfate and aqueous solution of potassium peroxydisulfate are respectively used as a surfactant and a polymerization catalyst for comparison, since it is the basic principle in the separating material according to the present invention that an aqueous emulsion of a polymer comprising methacrylic ester, acrylic ester, or acrylonitrile alone, or a mixed solution of two or more thereof, is applied, it may be used in combination with other catalysts and surfactants in the actual polymerization. The separating materials shown in the examples were subjected to emulsion polymerization unless otherwise specifically indicated. However, it should not be construed that the present invention is limited to the content of the polymer or copolymer contained in the aqueous emulsion obtained according to this method.

Common conditions (1) Polymerization Method of Separating material

1 A separable flask with a volume of 500 ml, having a stirrer, a reflux condenser and a dropping funnel equipped therewith, is used. This flask is charged with 155 ml of distilled water and 0.75 g of sodium lauryl sulfate for dissolution and purged with nitrogen.

2 110 g of each monomer alone or a mixed solution of monomers and 10 ml of a 6.0% by weight potassium peroxydisulfate aqueous solution are prepared. They are hereinafter designated as a monomer solution and a catalyst solution, respectively.

3 The flask is charged with 20 g of the monomer solution and 1 ml of the catalyst solution, and the solution temperature in the flask is adjusted at 70° C. on a water bath.

4 After 30 minutes, when the solution has become white, the remaining monomer solution is added dropwise from the dropping funnel over 2 hours. Meanwhile, the remaining catalyst solution is dividedly added. In the case that the first added monomer solution has not yet become white in 30 minutes, the solution temperature in the flask is raised to 80° C. to effect the polymerization.

5 After two hours, all of the monomer solution and the catalyst solution are added, and the polymerization is continued for an additional one hour.

6 The stirring is stopped, and the solution temperature is returned to room temperature to obtain an aqueous emulsion. In case that an acidic monomer is copolymerized, the solution is made neutral with 30% by weight ammonia water.

(2) Evaluation Method of Effects of Separating Material

1 A denture is prepared by using a denture base material, trade mark "Acron" (available from GC Corporation).

2 Each separating material is applied to the mucosal surface of the denture and dried by an air gun, if desired.

3 A tissue conditioner, trade mark "Soft Liner" a two component resinous material containing a powder component, which is extremely fine acrylic resin, and a liquid component which is a mixture of a plasticizer and an alcohol, which is (available from GC Corporation) is mixed therewith and piled up on the mucosal surface of the denture. After 10 minutes, this sample is immersed in water at 37° C. There are thus prepared 12 samples.

4 After 1 day, 7 days and 14 days, the samples are taken out from water 4 samples respectively, the tissue conditioner is slowly peeled off from the denture by hand, and the state of the tissue conditioner attached to the mucosal surface is then observed. The case that "Soft Liner" is completely peeled off from the denture surface, the case that a part of "Soft Liner" is torn off and left on the denture surface, and the case that the whole of "Soft Liner" is torn off and left on the denture surface, are evaluated as "A", "B", and "C", respectively. Then, the number of the corresponding pieces in each case is counted. The results obtained are shown in Table 1.

(3) Evaluation Method of Film-Forming properties of Separating Meterial

1 A denture base material, trade mark "Acron" is polymerized and formed into a size of 40 mm×40 mm×2 mm.

2 Each separating material is applied to the mucosal surface of the denture in a thermostatic chamber at 23° C. and allowed to stand for one hour. There are thus prepared four pieces for each sample.

3 The case that a transparent coating film is obtained and the case that a transparent coating film is not obtained are evaluated as "A" and "B", respectively. Then, the number of the corresponding pieces in each case is counted. The results obtained are also shown in Table 1.

EXAMPLE 1

The following monomer solution was polymerized and provided for the tests.

| | |
|---|---|
| Acrylonitrile | 0.48 (molar ratio) |
| n-Butyl acrylate | 0.48 |
| Acrylic acid | 0.04 |

EXAMPLE 2

The following monomer solution was polymerized and provided for the tests.

| | |
|---|---|
| Ethyl methacrylate | 0.43 (molar ratio) |
| n-Butyl acrylate | 0.43 |
| Acrylic acid | 0.14 |

EXAMPLE 3

The following monomer solution was polymerized and provided for the tests.

| | |
|---|---|
| Ethyl methacrylate | 0.46 (molar ratio) |
| Lauryl methacrylate | 0.09 |
| n-Butyl acrylate | 0.41 |
| Acrylic acid | 0.04 |

EXAMPLE 4

The following monomer solution was polymerized and provided for the tests.

| Methyl methacrylate | 0.30 (molar ratio) |
| 2-Ethylhexyl acrylate | 0.54 |
| Acrylic acid | 0.08 |
| 2-hydroxyethyl methacrylate | 0.08 |

EXAMPLE 5

The following monomer solution was polymerized and provided for the tests.

| n-Butyl methacrylate | 0.97 (molar ratio) |
| Dibutyl phthalate (5.7% by weight) | 0.03 |

EXAMPLE 6

The following monomer solution was polymerized and provided for the tests,

| Ethyl acrylate | 0.95 (molar ratio) |
| Acrylic acid | 0.05 |

EXAMPLE 7

The following monomer solution was polymerized and provided for the tests.

| n-Butyl methacrylate | 0.40 (molar ratio) |
| 2-Ethylhexyl acrylate | 0.55 |
| Sodium 2-sulfoethyl methacrylate | 0.05 |

EXAMPLE 8

The following monomer solution was polymerized and provided for the tests.

| Acrylonitrile | 0.48 (molar ratio) |
| n-Butyl acrylate | 0.48 |
| Acrylic acid | 0.04 |

COMPARATIVE EXAMPLE 1

"Soft Liner" was piled direct on a denture.

COMPARATIVE EXAMPLE 2

Vaseline was applied to a denture.

COMPARATIVE EXAMPLE 3

A cyclohexane solution containing 50% by weight of vaseline was applied to a denture.

COMPARATIVE EXAMPLE 4

The following monomer solution was polymerized and provided for the tests,

| Methyl methacrylate | 0.43 (molar ratio) |
| n-Butyl methacrylate | 0.43 |
| Acrylic acid | 0.14 |

COMPARATIVE EXAMPLE 5

The following monomer solution was polymerized and provided for the tests,

| 2-Ethylhexyl acrylate | 0.47 (molar ratio) |
| n-Butyl methacrylate | 0.47 |
| Acrylic acid | 0.06 |

COMPARATIVE EXAMPLE 6

The following monomer solution was polymerized and provided for the tests.

| Ethyl methacrylate | 0.11 (molar ratio) |
| n-Butyl methacrylate | 0.85 |
| Acrylic acid | 0.04 |

COMPARATIVE EXAMPLE 7

Only 8.7 g of the following monomer solution as shown in Example 1 was polymerized and provided for the tests.

| Acrylonitrile | 0.48 (molar ratio) |
| n-Butyl acrylate | 0.48 |
| Acrylic acid | 0.04 |

TABLE 1

(Effects of Separating Material)

| | Film-Forming Properties | | Separating Effect | | |
|---|---|---|---|---|---|
| | A | B | A | B | C |
| Example 1 | | | | | |
| After 1 day | 4 | 0 | 4 | 0 | 0 |
| After 7 days | — | — | 4 | 0 | 0 |
| After 14 days | — | — | 4 | 0 | 0 |
| Example 2 | | | | | |
| After 1 day | 4 | 0 | 4 | 0 | 0 |
| After 7 days | — | — | 4 | 0 | 0 |
| After 14 days | — | — | 4 | 0 | 0 |
| Example 3 | | | | | |
| After 1 day | 4 | 0 | 4 | 0 | 0 |
| After 7 days | — | — | 4 | 0 | 0 |
| After 14 days | — | — | 4 | 0 | 0 |
| Example 4 | | | | | |
| After 1 day | 4 | 0 | 4 | 0 | 0 |
| After 7 days | — | — | 4 | 0 | 0 |
| After 14 days | — | — | 4 | 0 | 0 |
| Example 5 | | | | | |
| After 1 day | 4 | 0 | 4 | 0 | 0 |
| After 7 days | — | — | 4 | 0 | 0 |
| After 14 days | — | — | 4 | 0 | 0 |
| Example 6 | | | | | |
| After 1 day | 4 | 0 | 4 | 0 | 0 |
| After 7 days | — | — | 4 | 0 | 0 |
| After 14 days | — | — | 4 | 0 | 0 |
| Example 7 | | | | | |
| After 1 day | 4 | 0 | 4 | 0 | 0 |
| After 7 days | — | — | 4 | 0 | 0 |
| After 14 days | — | — | 4 | 0 | 0 |

TABLE 1-continued (Effects of Separating Material)

| | Film-Forming Properties | | Separating Effect | | |
|---|---|---|---|---|---|
| | A | B | A | B | C |
| Example 8 | | | | | |
| After 1 day | 4 | 0 | 4 | 0 | 0 |
| After 7 days | — | — | 4 | 0 | 0 |
| After 14 days | — | — | 4 | 0 | 0 |
| Comparative Example 1 | | | | | |
| After 1 day | — | — | 0 | 0 | 4 |
| After 7 days | — | — | 0 | 0 | 4 |
| After 14 days | — | — | 0 | 0 | 4 |
| Comparative Example 2 | | | | | |
| After 1 day | — | — | 1 | 2 | 1 |
| After 7 days | — | — | 1 | 2 | 1 |
| After 14 days | — | — | 1*a | 1 | 2 |
| Comparative Example 3 | | | | | |
| After 1 day | — | — | 1 | 2 | 1 |
| After 7 days | — | — | 0 | 2 | 2 |
| After 14 days | — | — | 0 | 1 | 3 |
| Comparative Example 4 | | | | | |
| After 1 day | 0 | 4 | — | — | — |
| After 7 days | — | — | — | — | — |
| After 14 days | — | — | — | — | — |
| Comparative Example 5 | | | | | |
| After 1 day | 4 | 0 | 4*b | 0 | 0 |
| After 7 days | — | — | 4*b | 0 | 0 |
| After 14 days | — | — | 4*b | 0 | 0 |
| Comparative Example 6 | | | | | |
| After 1 day | 4 | 0 | 4*b | 0 | 0 |
| After 7 days | — | — | 4*b | 0 | 0 |
| After 14 days | — | — | 4*b | 0 | 0 |
| Comparative Example 7 | | | | | |
| After 1 day | 4*c | 0 | 1 | 3 | 0 |
| After 7 days | — | — | 1 | 3 | 0 |
| After 14 days | — | — | 1 | 3 | 0 |

[Note]
*a: "Soft Liner" was dropped from the denture.
*b: A part of "Soft Liner" was peeled off from the denture.
*c: The separating material was repelled by the denture so that the application was difficult.
—: Not corresponding thereto.

A tissue conditioner lined on a denture is frequently exchanged at intervals between several days and one week. Since the tissue conditioner is well adhered to the denture, its removal operation from the denture was greatly difficult. If the denture base separating material according to the present invention is used, since the tissue conditioner can be readily separated by hand, the removal operation is extremely easy so that the examination efficiency is markedly improved. Moreover, since the denture base separating material according to the present invention has an appropriate adhesion, there is no fear that the tissue conditioner is peeled off from the denture during the use of the denture in the oral cavity. While the denture base separating material according to the present invention is cloudy at the time when it is applied to the denture, it becomes a transparent coating film after drying by means of an air gun or the like. For this reason, it is easy to confirm a portion where the denture base separating material according to the present invention is applied, and it is also possible to continue the degree of drying. Furthermore, the denture base separating material according to the present invention does not contain an organic solvent, not only it is free from malodors, but it does not generate cracks, dry spots and the like on the denture surface.

While the invention has been described in detail and with reference to specific embodiments thereof, it will be apparent to one skilled in the art that various changes and modifications can be made therein without departing from the spirit and scope thereof.

What is claimed is:

1. A method for adhering a tissue conditioner with a denture base material such that said tissue conditioner is firmly fixed to said denture base, but readily removed manually after use, the method comprising:

applying to a denture base material a film of a separating material comprising an aqueous emulsion obtained by emulsion polymerization of a methacrylic ester, an acrylic ester, or an acrylonitrile alone, or a mixture of two or more thereof, in the presence of a water-soluble radical polymerization initiator and a surfactant, K the monomer composition being adjusted to provide a minimum film forming temperature (MFT) of 23° C. or lower; and applying a polymer soft liner tissue conditioner to said film.

2. A method for adhering a tissue conditioner with a denture base material such that said tissue conditioner is firmly fixed to said denture base, but readily removed manually after use, the method comprising:

applying to a denture base material a film of a separating material comprising an aqueous emulsion obtained by emulsion polymerization of a methacrylic ester, an acrylic ester, or an acrylonitrile alone, or a mixed solution of two or more thereof, in the presence of a water-soluble radical polymerization initiator and a surfactant, and containing 7 parts or less by weight, based on 100 parts by weight of the polymer contained in said aqueous emulsion, of a phthalic ester or a fatty acid ester, the monomer composition being adjusted to provide a minimum film forming temperature (MFT) of 23° C. or lower; and applying a polymer soft liner tissue conditioner to said film.

3. The method of claim 1, wherein said aqueous emulsion contains an amount of polymer of from 8 to 55 % by weight.

4. The method of claim 2, wherein said aqueous emulsion contains an amount of polymer of from 8 to 55 % by weight.

* * * * *